United States Patent
Lizardi (10) Patent No.: US 10,667,803 B2
(45) Date of Patent: Jun. 2, 2020

(54) SYSTEMS AND METHODS FOR REPAIRING TISSUE

(71) Applicant: Medos International Sàrl, Le Locle (CH)

(72) Inventor: Jose E. Lizardi, Walpole, MA (US)

(73) Assignee: MEDOS INTERNATIONAL SÀRL, Le Locle (CH)

( * ) Notice: Subject to any disclaimer, the term of this patent is extended or adjusted under 35 U.S.C. 154(b) by 83 days.

(21) Appl. No.: 15/232,303

(22) Filed: Aug. 9, 2016

(65) Prior Publication Data

US 2016/0345955 A1 Dec. 1, 2016

Related U.S. Application Data

(62) Division of application No. 13/331,322, filed on Dec. 20, 2011, now Pat. No. 9,439,644.

(51) Int. Cl.
*A61B 17/04* (2006.01)

(52) U.S. Cl.
CPC .. *A61B 17/0401* (2013.01); *A61B 2017/0403* (2013.01); *A61B 2017/0404* (2013.01); *A61B 2017/0406* (2013.01); *A61B 2017/0409* (2013.01); *A61B 2017/0412* (2013.01); *A61B 2017/0417* (2013.01); *A61B 2017/0419* (2013.01); *A61B 2017/0445* (2013.01); *A61B 2017/0448* (2013.01); *A61B 2017/0458* (2013.01); *A61B 2017/0461* (2013.01); *A61B 2017/0475* (2013.01)

(58) Field of Classification Search
CPC .......... A61B 17/0401; A61B 17/12009; A61B 2017/0409; A61B 2017/0496; A61B 2017/0475; A61B 2017/0477; A61B 2017/0446; A61B 2017/0448; A61B 2017/0458; A61F 2002/0858
USPC .......... 606/139, 144, 148, 232, 304
See application file for complete search history.

(56) References Cited

U.S. PATENT DOCUMENTS

| | | | |
|---|---|---|---|
| 6,156,039 A | 12/2000 | Thal | |
| 6,520,980 B1 * | 2/2003 | Foerster | A61B 17/0401 606/232 |
| 7,887,551 B2 | 2/2011 | Bojarski et al. | |
| 8,337,525 B2 | 12/2012 | Stone et al. | |
| 8,821,543 B2 * | 9/2014 | Hernandez | A61B 17/0401 606/232 |
| 9,439,644 B2 | 9/2016 | Lizardi | |
| 2005/0187577 A1 | 8/2005 | Selvitelli et al. | |
| 2006/0190042 A1 | 8/2006 | Stone et al. | |
| 2006/0247641 A1 | 11/2006 | Re et al. | |
| 2007/0225719 A1 * | 9/2007 | Stone | A61B 17/0401 606/232 |

(Continued)

OTHER PUBLICATIONS

U.S. Appl. No. 13/331,322, filed Dec. 20, 2011, Systems and Methods for Repairing Tissue.

*Primary Examiner* — Sarah W Aleman (57) ABSTRACT

Devices and methods for anchoring tissue to bone are provided herein. In various embodiments, the tissue anchor systems and methods can provide a length of suture having terminal ends coupled to one another via a sliding knot so as to define a suture loop having an adjustable length. After passing a portion of the suture loop through a damaged tissue and coupling the suture loop to bone, the sliding knot can be advanced to shorten the suture loop in order to secure the tissue to bone.

12 Claims, 9 Drawing Sheets

(56) References Cited

U.S. PATENT DOCUMENTS

| | | |
|---|---|---|
| 2008/0065114 A1 | 3/2008 | Stone et al. |
| 2009/0281581 A1 | 11/2009 | Berg |
| 2009/0306711 A1* | 12/2009 | Stone ................ A61B 17/0401 606/232 |
| 2010/0249809 A1 | 9/2010 | Singhatat et al. |
| 2010/0256677 A1 | 10/2010 | Albertorio et al. |
| 2011/0022061 A1 | 1/2011 | Orphanos et al. |
| 2011/0077667 A1 | 3/2011 | Singhatat et al. |
| 2011/0270306 A1* | 11/2011 | Denham ............ A61B 17/0401 606/228 |
| 2012/0296375 A1 | 11/2012 | Thal |
| 2013/0158598 A1 | 6/2013 | Lizardi |

* cited by examiner

SYSTEMS AND METHODS FOR REPAIRING TISSUE

CROSS-REFERENCED TO RELATED APPLICATIONS

This application claims priority to U.S. Non-Provisional application Ser. No. 13/331,322, filed Dec. 20, 2011, and entitled "SYSTEMS AND METHODS FOR REPAIRING TISSUE," which is incorporated by reference in its entirety.

FIELD OF USE

The present disclosure relates to devices and methods for repairing tissue, in particular to suture anchoring devices and methods for anchoring tissue to bone.

BACKGROUND

A variety of injuries and conditions require repair of soft tissue damage, or reattachment of soft tissue to bone and/or surrounding tissue. For example, when otherwise healthy tissue has been torn away from a bone, such as a shoulder rotator cuff tendon being partially or completely torn from a humerus (a rotator cuff tear), surgery is often required to reattach the tissue to the bone, to allow healing and reattachment to occur. A number of devices and methods have been developed for performing these surgical repairs, some of the more successful methods include the use of suture anchors, which typically include an anchor body having one or more suture attachment features, and a tissue or bone engaging feature for retaining the suture anchor within or adjacent to the tissue or bone. Depending on the specific injury, one or more suture anchors connected to, or interconnected by, one or more segments of suture, is used to perform the repair.

Surgery can also be required when a tear occurs in the substance of a single type of tissue, for example in the meniscus of the knee (a meniscal tear). One method of repairing such a tear is to stitch it closed by passing a length of suture through the tissue and tying the suture. Suture can also be used in conjunction with one or more suture anchors to repair such tissue tears. Sutures can be fastened to suture anchors and to tissue using knots tied by the surgeon during a repair procedure. In minimally invasive procedures, however, the surgeon must use tools inserted through a small diameter cannula or access portal, which can make the knotting process difficult and tedious.

Accordingly, there remains a need for improved methods and devices for repairing torn or damaged tissue, and in particular for methods and devices suitable for arthroscopic repair of torn or otherwise damaged tissue using suture anchors.

SUMMARY

Systems and methods for repairing damaged tissue, and particularly for anchoring tissue to bone, are provided herein. As described below, the systems and methods can utilize a suture having terminal ends coupled to one another by a sliding knot (e.g., a pre-formed knot) that can be advanced by a surgeon to secure a tissue to a bone anchor. Various systems and methods in accord with the teachings herein can be effective to facilitate the surgical techniques for reattaching soft tissue to bone. One example of such a technique is the repair of shoulder instability resulting from a damaged labrum.

Various aspects of methods for anchoring tissue to bone are disclosed herein. In a first aspect, the method includes utilizing a length of suture having terminal ends attached to one another by a sliding knot. The length of suture defines a loop having a first engagement member slidably disposed thereon at a location remote from the sliding knot. The first engagement member and a first portion of the loop can be advanced through tissue at a first location within a patient's body. With the first portion of the loop extending through the tissue, the first engagement member can be withdrawn to a position outside of the patient's body. The method also includes coupling the first engagement member to a bone anchor, for example, after withdrawing the first engagement member. The bone anchor, with the first engagement member coupled thereto, is implanted in bone. The method also includes advancing the sliding knot along the suture and toward the tissue to anchor the tissue to bone.

In some aspects, the method can include, after advancing the sliding knot, cutting the terminal ends of the suture extending from the sliding knot. In various embodiments, the method can include tensioning the suture. In some embodiments, the method can also include drilling a bone hole that is configured to receive the bone anchor therein.

In one aspect, the sliding knot and the first engagement member are disposed on opposed sides of the tissue, for example, when the tissue is secured to the bone anchor. In some embodiments, the sliding knot and the bone anchor are disposed on opposed sides of the tissue.

In various embodiments, the loop can have a second engagement member slidably disposed thereon at a location between the first engagement member and the sliding knot. In such an aspect, the method can include, for example, advancing the second engagement member and a second portion of the loop through the tissue at a second location within a patient's body adjacent to the first location, withdrawing the second engagement member to a position outside of the patient's body with the second portion of the loop extending through the tissue, and coupling the second engagement member to the bone anchor. In various embodiments, a portion of the loop between the first and second engagement members can be disposed on an opposed side of the tissue from the first and second engagement members after the first and second engagement members are advanced through the tissue. In one aspect, the method can include inserting each of the first and second engagement members into a needle prior to advancing the first and second engagement members through tissue such that the engagement members can be advanced through tissue by inserting each needle through the tissue at a desired location.

The engagement members can have a variety of configurations and can be coupled to the bone anchor in a variety of manners. For example, each of the first and second engagement members can comprise opposed first and second surfaces and two bores extending therebetween. In one aspect, the first and second engagement members are coupled to the bone anchor by threading a portion of suture extending from the first and second engagement members through the bone anchor. For example, the first and second engagement members can be coupled to the bone anchor by threading the first and second engagement members through a lumen extending from a proximal end to a distal end of the bone anchor. By way of example, the second engagement member can be coupled to the bone anchor after withdrawing the first engagement member. In some embodiments, the second engagement member is not advanced through the tissue prior to being coupled to the bone anchor.

In one aspect, the bone anchor can be implanted with the first and second engagement members disposed therein. Alternatively, the bone anchor can be implanted with the first and second engagement members disposed adjacent to the distal end of the bone anchor.

In one aspect, a method for anchoring tissue to bone is provided that includes utilizing a suture loop having terminal ends attached to one another by a sliding knot and advancing a first segment of the loop through tissue at a first location within a patient's body. The method also includes withdrawing a portion of the first segment of the loop to a position outside of the patient's body with the first segment of the loop extending through the tissue. The first segment of the loop is coupled to a bone anchor, for example, after withdrawing the first segment of the loop. The method also includes coupling a second segment of the loop to the bone anchor and implanting the bone anchor, with the first and second segments coupled thereto, in bone. The sliding knot is advanced toward the tissue to shorten the suture loop.

In various embodiments, the first and second segments can be coupled to the bone anchor by threading the first and second segments through the bone anchor.

These and other aspects of the presently disclosed methods and systems are detailed below.

BRIEF DESCRIPTION OF THE DRAWINGS

The presently disclosed embodiments will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Devices and methods for repairing torn or damaged tissue are provided herein. Various aspects of devices and methods in accord with the present teachings can enable a surgeon to quickly and consistently repair tissue separations (e.g., the detachment of a labrum from the glenoid rim), while reducing the time spent tying complex surgical knots within the limited confines typical of arthroscopic procedures. It is to be understood that particular devices and methods disclosed herein are exemplary and not limiting of the present invention. For example, embodiments illustrated for reattaching a detached or torn tendon or ligament to bone can be similarly applied for repairing in-substance injuries to soft tissue, such as the meniscus of the knee, and the labrum of the hip joint.

Tissue anchor systems and methods in accord with the present teachings generally utilize a length of suture having terminal ends coupled to one another so as to define a suture loop having an adjustable length. After passing a portion of the suture loop through a damaged tissue (e.g., a detached labrum) and coupling the suture loop to bone (e.g., the glenoid), the suture loop can be shortened to reattach the damaged tissue.

Figure 1:
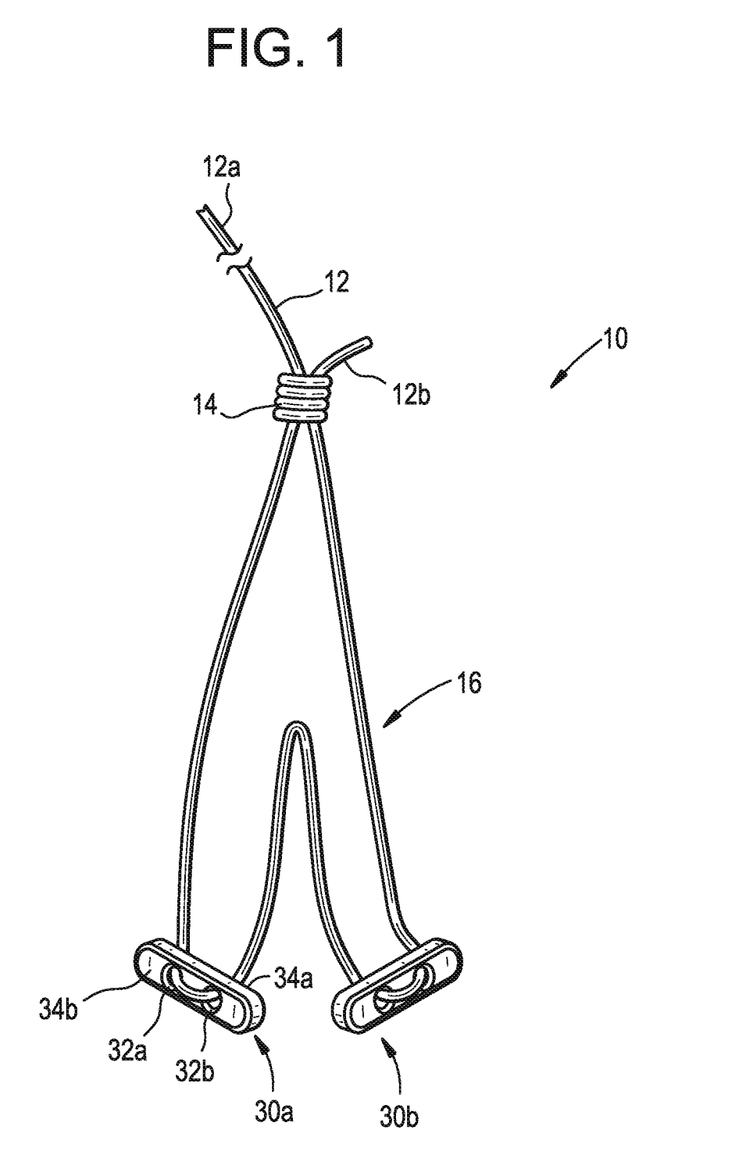
FIG. 1 is a perspective view of an exemplary embodiment of a tissue anchor system in accord with the teachings herein.
Figure 2:
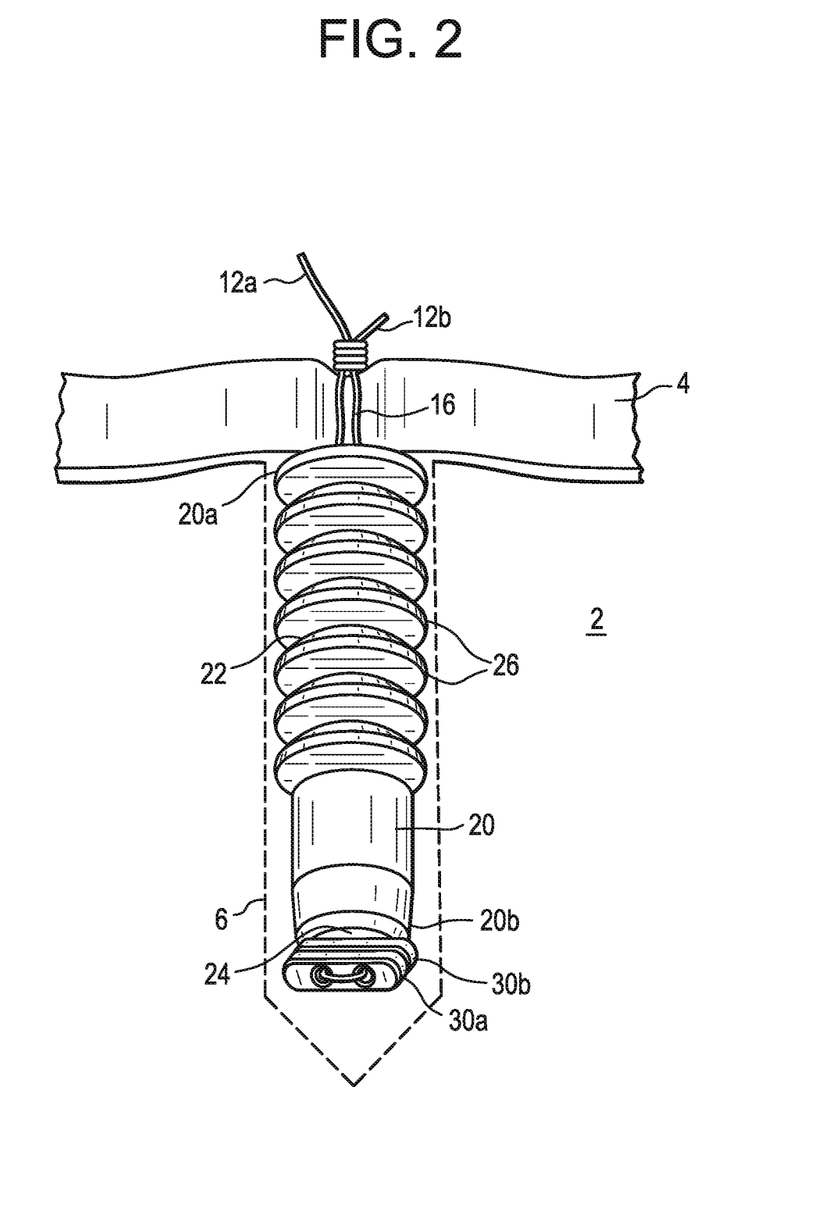
FIG. 2 is a perspective view of the tissue anchor system of FIG. 1 coupled to an exemplary bone anchor disposed within a bone hole.

Referring now to the figures, an exemplary embodiment of a tissue anchor system 10 in accord with the present teachings is shown in FIG. 1. The tissue anchor system 10 generally includes a length of suture 12 having terminal ends 12a,b coupled to one another by a sliding knot 14 so as to define a suture loop 16 having an adjustable length. In the exemplary embodiment depicted in FIG. 1, the tissue anchor system 10 can additionally include one or more engagement members 30a,b slidably coupled to the suture loop 16. As shown in FIG. 2, the engagement members 30a,b can be coupled to a bone anchor 20 fixed within a bone tunnel 6, for example, so as to couple the tissue anchor system 10 to bone 2. The sliding knot 14 can be advanced to shorten the suture loop 16, thereby fixing the tissue 4 to bone 2.

Though generally referred to as a "suture" herein, the suture 12 can comprise any elongate element suitable for implantation and use in making surgical repairs. A person skilled in the art will appreciate that the suture 12 can be formed from a variety of materials. By way of example, sutures for use in accord with the present teachings can be fabricated from natural materials (e.g., silk) and/or synthetic materials, such as polypropylene, polyethylene terephthalate (PET) or other polyester materials. Moreover, the suture material can be selected such that the suture 12 is absorbable (e.g., Panacryl® and Vicryl®, both manufactured by Ethicon, Inc., a Johnson and Johnson company) or non-absorbable (e.g., Ethibond®, also manufactured by Ethicon, Inc.). A partially absorbable suture for use with the systems and methods disclosed herein can include both a non-absorbable component (e.g., polyethylene) and an absorbable component (e.g., polydioxanone), for example. As will be appreciated by a person skilled in the art, sutures for use in accord with the teachings herein can have any cross-sectional shape, for example, a circular or non-circular cross-section, or any size, for example, a #2 suture or other suture of larger or smaller diameter.

In various embodiments, the terminal ends 12a,b of the suture 12 can be coupled to one another so as to define a suture loop 16. As will be discussed in detail below, a first terminal end 12a of the suture 12 can serve as a free end that can be actuated to tension the suture 12, while the second terminal end 12b can be movably coupled to a portion of the suture 12 so as to define a suture loop 16.

While a variety of techniques can be used to movably couple the terminal ends 12a,b of the suture 12, in an exemplary embodiment a sliding knot is provided to enable the suture loop 16 to be shortened and/or the suture 12 to be tensioned, for example, by pulling on at least one of the terminal ends 12a,b. By way of example, the knot 14 can be virtually any type of locking or non-locking sliding knot. As will be appreciated by a person skilled in the art, non-locking sliding knots (e.g., the Duncan loop, Tennessee Slider, and Roeder knot) can be tensioned and subsequently locked to prevent slipping. By way of example, one or more additional loops can be thrown on top of the sliding knot 14 after the tissue has been positioned and the desired tension is placed on the suture 12. A locking sliding knot (e.g., Midshipman's Hitch and the Weston knot) can also be used in accord with the methods and systems described herein. By way of example, a locking sliding knot can be locked following proper tensioning of the suture by selectively applying tension in an appropriate sequence to the terminal ends 12a,b of the suture 12. Regardless of the technique used to couple the first and second terminal ends 12a,b, at least one of the terminal ends can extend from the knot 14 to form a trailing end that can be used for applying tension to the suture 12 and/or decreasing the length of the suture loop 16.

The tissue anchor system 10 can be secured to bone using a variety of devices and techniques. By way of example, the suture 12 can be coupled to a bone anchor that is implanted at a selected surgical reattachment site. Bone anchors for use with the tissue anchor systems and methods disclosed herein are generally configured to securely engage bone so as to provide a point of attachment for the tissue anchor system 10 and can have any number of configurations. As will be appreciated by a person skilled in the art, a variety of prior art bone anchors modified in light of the teachings herein can be used to secure the tissue anchor system to bone. As will be discussed in detail below, in various embodiments, the suture loop 16 can be coupled directly to a bone anchor, or in the alternative, can be indirectly coupled to a bone anchor via the coupling of the suture with an engagement member, which in turn can be coupled to the bone anchor.

With reference now to FIG. 2, an exemplary embodiment of a bone anchor 20 is depicted in a bone tunnel 6. As shown in FIG. 2, the bone anchor 20 can have a generally cylindrical elongate body 22 extending between a proximal end 20a and a tapered distal end 20b that can facilitate entry into the bone tunnel 6. A lumen 24 can extend between the proximal and distal ends 20a,b. In various aspects discussed in detail below, the lumen 24 can be configured to receive a portion of the suture loop 16 and/or engagement members 30a,b.

In various embodiments, the bone anchor 20 can additionally include one or more bone-engaging features that can aid in securing the bone anchor 20 to bone (e.g., within a bone tunnel). As will be appreciated by a person skilled in the art, various bone-engaging features can be utilized, including, for example, barbs, teeth, threads, protrusions, etc. As depicted in FIG. 2, for example, the bone anchor 20 can include a plurality of ridges 26 formed on its external surface. As will be appreciated by a person skilled in the art, the ridges 26 can allow the bone anchor 20 to be forced distally (e.g., pushed) into the bone tunnel 6, for example, and can prevent the bone anchor 20 from backing out of the bone.

Bone anchors for use in systems and methods described herein can also have a variety of configurations, shapes, and sizes, and can be formed from a variety of materials. By way of example, the bone anchor 20 can be configured to be implanted within a bone tunnel 6, and can have a size and shape that allows it to be fully engaged with the bone tunnel wall through the thickness of the cortical bone at the implantation site. As will be appreciated by a person skilled in the art, the proximal end 20a of the anchor 20 can include features that enable engagement with a deployment device (e.g., driver) for implanting the bone anchor 20 into bone. Moreover, the physical properties of the material of which the bone anchor is formed can be sufficient to allow the bone anchor to be driven or screwed into the bone tunnel 6, for example, without damaging the bone anchor 20. Likewise, the material can have sufficient strength so as to resist pull out, for example, when proximal tension is applied to the bone anchor 20 or a suture coupled thereto. As will be appreciated by a person skilled in the art, bone anchors 20 for use in accord with the teachings herein can be bioabsorbable and/or osteoconductive such that the bone anchor 20 can promote healing and/or ingrowth of native tissue.

In various embodiments disclosed herein, the suture 12 can be coupled directly to a bone anchor 20, or alternatively, can be indirectly coupled to a bone anchor 20 via the coupling of the suture with an engagement member, which in turn, can be coupled to the bone anchor 20. For example, with reference now to FIG. 3, there is depicted an exemplary embodiment of a bone anchor 320 having a suture-engaging element configured to engage a suture loop 316 directly. As will be appreciated by the person skilled in the art, suture-engaging elements can be adapted to engage one or more suture loops 316 that extend through the inner lumen 324 of the suture anchor 320 and can have a variety of configurations.

Figure 3:
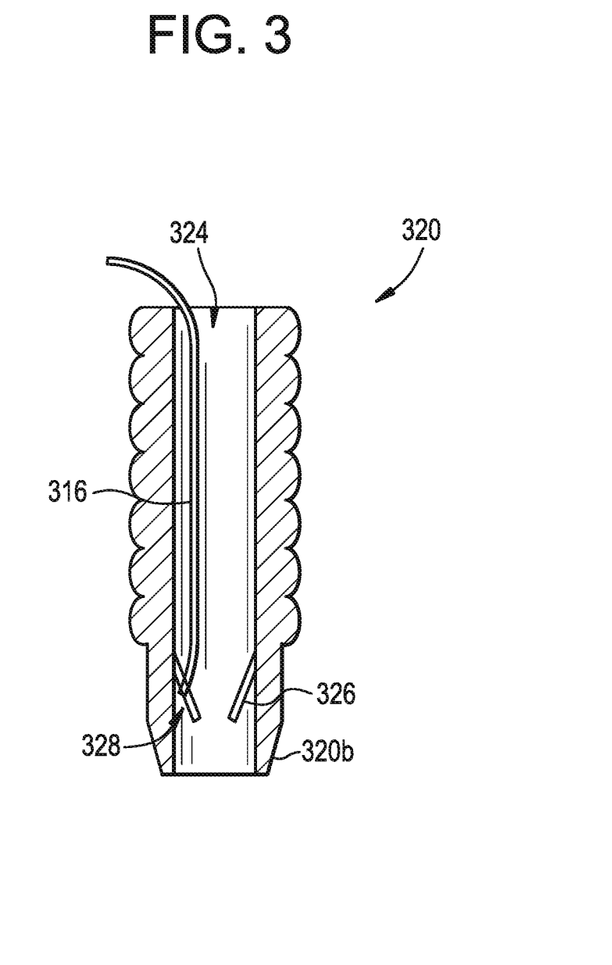
FIG. 3 is a cross-sectional view of another exemplary embodiment of a bone anchor.

As shown in FIG. 3, for example, the bone anchor 320 can include a suture-engaging post 326 extending from a sidewall of the lumen 324. The angular orientation of the post 326 relative to a longitudinal axis of the bone anchor can vary, but in an exemplary embodiment the post 326 can extend from the sidewall towards the distal end 320b of the bone anchor 320. In such a manner, proximal tension on a suture loop 316 extending distally beyond the post 326 can be effective to pull the suture loop 316 within a suture-receiving cavity 328 between the post 326 and the sidewall of the lumen 324.

Though the suture-engaging post 326 is depicted as being positioned adjacent to the distal end 320b of the bone anchor 320, a suture-engaging element can be positioned at any position along the length of the bone anchor 320 that is effective to couple a suture loop 316 to the bone anchor 320. A person skilled in the art will further appreciate that the suture-engaging element can be integrally formed with the bone anchor 320 (i.e., the bone anchor 320 and the suture-engaging element can be molded as a single unit or formed from a single piece of material), or the suture-engaging element can be fixedly or removably mated to the bone anchor 320. One skilled in the art will appreciate that the anchor 320 can have features other than lumen 324 or suture-engaging post 326 to couple to a suture. For example, a transverse bore (not shown) can be formed in the bone anchor 320 to receive a suture.

As mentioned above, the suture can be coupled indirectly to a bone anchor. In various embodiments disclosed herein, the suture 12 can be indirectly coupled to a bone anchor via the coupling of the suture with an engagement member, which in turn, can be coupled to the bone anchor. As will be appreciated by a person skilled in the art, the engagement member(s) are generally configured to be coupled to both a suture and a bone anchor and can have a variety of configuration and.

With reference again to the exemplary tissue anchor system 10 depicted in FIG. 1, one or more engagement member(s) can be coupled to the suture loop 16. As shown in FIG. 1, the engagement members can comprise tabs 30a,b having a generally elongate body. One or more bores 32a,b configured to receive a tissue therethrough can extend between opposed first and second surfaces 34a,b of the tabs 30a,b.

The bores 32a,b can be configured to slidably receive a suture therethrough and can have a variety of configurations, sizes, and shapes. As will be appreciated by those skilled in the art, the bores 32a,b can be of any shape (e.g., circular, oval, etc.) and/or diameter capable of receiving a suture therein. As depicted in FIG. 1, for example, the junction of the opposed surfaces 34a,b and the bores 32a,b can be rounded so as to optimize the slidability of the suture 12 therethrough and among the respective openings. In some embodiments, the bores 32a,b can be angularly oriented relative to the opposed faces 34a,b so as to promote, for example, the angular displacement of a suture disposed therethrough. In such a manner, a suture 12 traversing the first bore 32a, for example, can be angularly guided toward the second bore 32b so as to reduce the profile of the suture 12 extending from the bores 32a,b and/or prevent kinking of the suture 12.

Though the tabs 30a,b appear identical in the exemplary embodiment depicted in FIG. 1, a person skilled in the art will appreciate that any number of engagement members having similar or different configurations from one another can be coupled to the suture loop 16. Similarly, any number of bores 32a,b having the same or different configurations from one another can extend through the tabs 30a,b. For example, each of the bores 32a,b can be substantially similar in shape (as shown) or they can each have a distinct shape and/or diameter.

The tabs 30a,b can have various features to enable coupling with the bone anchor 20. For example, with reference now to FIG. 2, the tabs 30a,b can be dimensioned so as to allow for their passage through the lumen of the bone anchor 20 in a first orientation. By way of non-limiting example, the tabs 30a,b can have a length in a range from about 1.5 mm to about 6 mm, a depth (i.e., the distance between opposed surfaces 34a,b) less than about 3 mm, and a width less than about 3 mm. After being threaded distally through the lumen 24 and exiting the distal end of the bone anchor 20, the tabs 30a,b can be rotated to a second orientation such that tension applied to a suture loop 16 coupled to the tabs 30a,b can draw the tabs 30a,b proximally into abutment with the distal end 20b of the bone anchor 20, as shown in FIG. 2, thereby preventing further proximal movement. In some embodiments, for example, the major dimension (e.g., length) of the tabs 30a,b can be oriented perpendicular to the bone anchor 20 and the axis of the bone hole 6 in the second orientation, and the tabs 30a,b can have a length equal to or less than the diameter of the bone hole.

Figure 5:
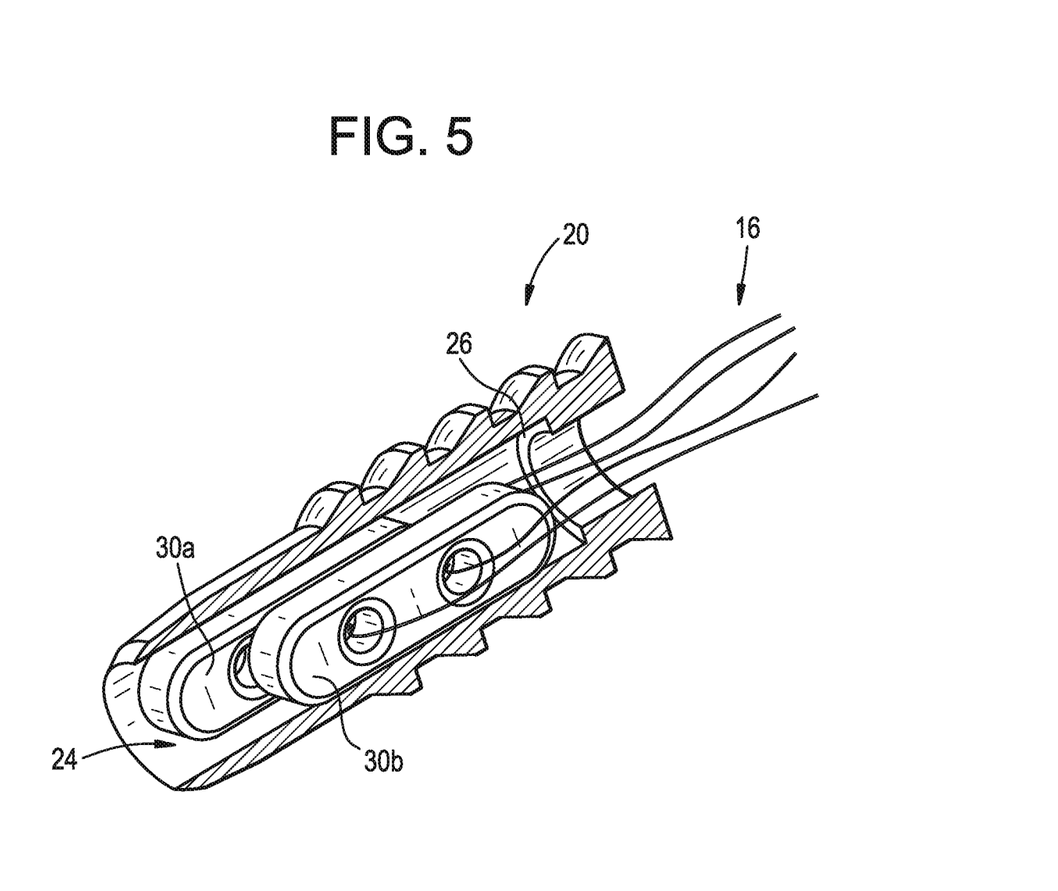
FIG. 5 is a cross-sectional view of an exemplary embodiment of a bone anchor.

Alternatively, in some embodiments, the bone anchor 20 can be configured to retain the tabs 30a,b within the lumen 24, rather than adjacent its distal end 20b. For example, with reference now to FIG. 5, an exemplary embodiment of a bone anchor configured to retain the tabs 30a,b therein is shown. The bone anchor 20 is substantially similar to that discussed above in reference to FIG. 2, but differs in that a shoulder 26 can be formed within the lumen 24 such that the diameter of the lumen 24 at its proximal end is smaller than that of its distal end. The relative dimensions of the lumen 24 and tabs 30a,b can ensure that only one of the tabs 30a,b can be passed through the proximal portion of the lumen 24 at a time, whereas the distal portion of the lumen 24 can accommodate both tabs 30a,b therein in a side-by-side manner. Accordingly, the tabs 30a,b can be loaded into the bone anchor 20 sequentially, and subsequently positioned side-by-side such the shoulder 26 can prevent either from being pulled out of the bone anchor 20, for example, by a proximal tension placed on the suture loop 16. By way of non-limiting example, the tabs 30a,b can have a length less than a length of the bone anchor 20 (e.g., 1 mm less than the length of the bone anchor 20) and a width and depth less than about 3 mm.

The present invention also provides methods for anchoring tissue to bone. FIGS. 4A-4E illustrate one exemplary method for anchoring tissue to bone in accordance with various aspects of the teachings herein. While virtually any tissue anchor system can be used to perform the techniques described herein, FIGS. 4A-4E illustrate the use of the above-described tissue anchor system 10 depicted in FIG. 1 for reattaching a detached labrum 4 to the glenoid 2 in the shoulder. A person skilled in the art will appreciate, however, that the tissue anchor systems and methods disclosed herein can be used for a variety of surgical procedures involving the reattachment of soft tissue. One skilled in the art will also appreciate that the system of the invention can be used with known and accepted arthroscopic surgical techniques, including patient preparation, anesthetization, and creation of one or more portals through a patient's skin. By way of example, a surgeon can select a location for reattachment of a detached labrum 4 to the glenoid 2 and the selected site can be prepared, for example, by drilling into the glenoid 2 a bone hole 6 for receiving a bone anchor 20.

One skilled in the art will appreciate that the methods disclosed herein are typically performed in an arthroscopic procedure in which the variety of instruments are passed through one or more cannulas or other access ports. While FIGS. 4a-4E illustrate various steps of an exemplary procedure, they do so without illustrating a cannula or other access port so as to provide more clarity to the illustration.

As otherwise discussed herein, a tissue anchor system 10 can be provided having a length of suture 12 having terminal ends 12a,b coupled to one another by a sliding knot 14 so as to define a suture loop 16. One or more engagement members 30a,b can be slidably coupled to the suture loop 16 and can be separated from one another and from the knot 14 by a portion of the suture loop 16, as depicted for example in FIG. 1. In some embodiments, the suture anchor system 10 can be delivered to the surgeon, for example, with the knot having been pre-tied.

Figure 4A:
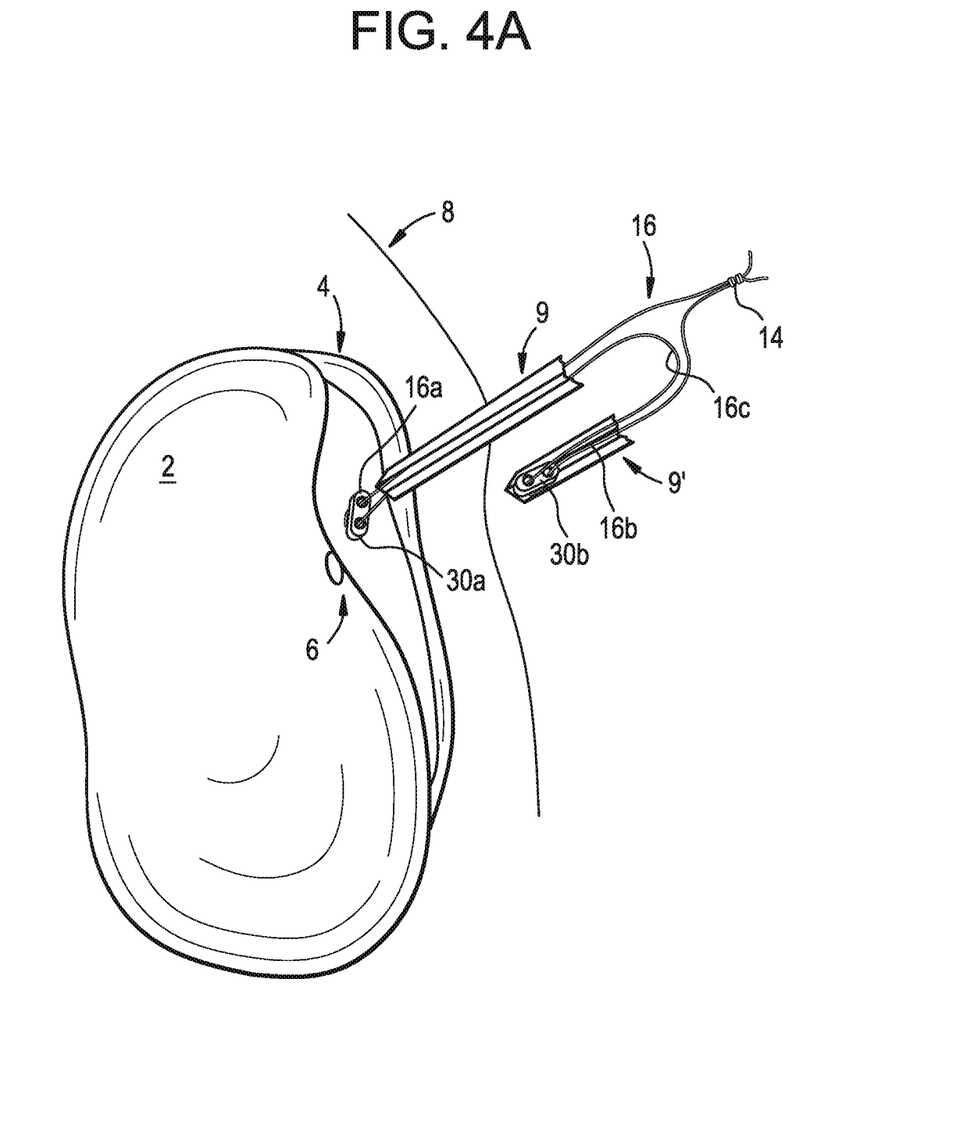
FIG. 4A is a representation of a first engagement member of the tissue anchor system of FIG. 1 being delivered to a surgical site in a shoulder joint.

Referring now to FIG. 4A, each of the tabs 30a,b and a portion of the suture loop 16 can be loaded into a delivery device configured to deliver the engagement members 30a,b into the body (e.g., through skin surface 8) and through the labrum 4. As will be appreciated by a person skilled in the art, the delivery device can comprise, for example, a needle 9 having a passageway that can slidably receive a tab 30a,b. The needle 9 can be inserted into the patient and through the labrum 4 to advance the tab 30a and a portion of the suture loop 16a through the labrum 4 at a desired location. The needle 9 can also include, for example, a trigger mechanism (not shown) that can selectively eject the tab 30a from the needle 9. In some embodiments, the sliding knot 14 can remain outside the body while advancing the tab 30a through the labrum 4.

Figure 4B:
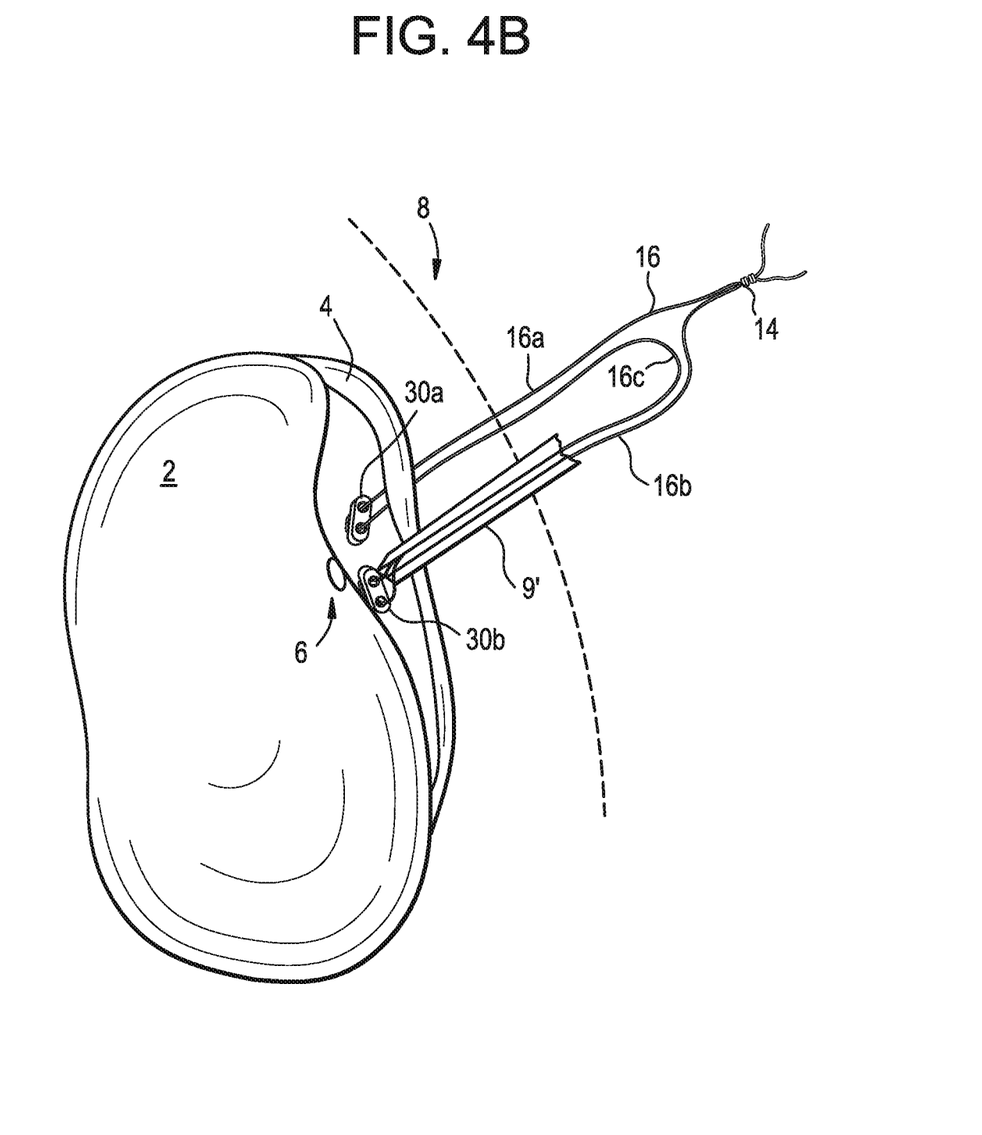
FIG. 4B is a representation of a second engagement member of the tissue anchor system of FIG. 1 being delivered to the surgical site.

In one exemplary embodiment, a second needle 9' can then be inserted into the patient through the same or different incision in the skin surface 8 and through the labrum 4 at a location adjacent to the first location to advance the tab 30b and a second portion of the suture loop 16b through the labrum 4, as shown in FIG. 4B, for example. With both tabs 30a,b advanced through the labrum 4, a portion of the suture loop 16c between the tabs 30a,b can remain disposed on the opposite side of the labrum 4 from the tabs 30a,b, for example, outside the body. In some embodiments, the sliding knot 14 can remain outside the body while advancing the tab 30b through the labrum 4.

Figure 4C:
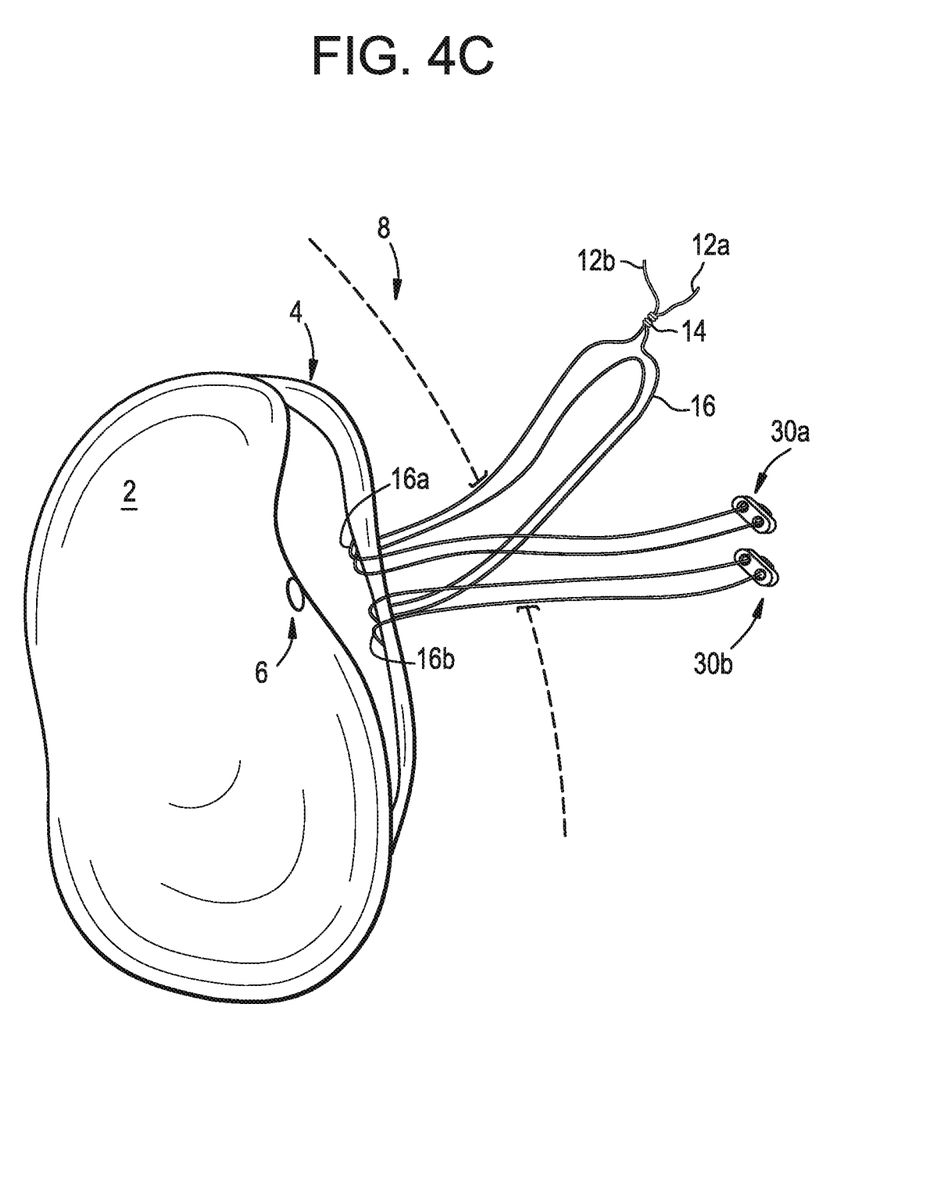
FIG. 4C is a representation of the first and second engagement members of the tissue anchor system of FIG. 1 being withdrawn to a location outside the body.

After advancing the tabs 30a,b through the labrum 4, the tabs 30a,b can be withdrawn from the body with each portion of the suture loop 16a,b extending through the labrum 4, as shown in FIG. 4C. The tabs 30a,b can then be removed from the joint and withdrawn from the body through the same or different incision(s) in the skin surface 8 which the needles 9, 9' were originally inserted through the skin surface 8. By way of example, a grasper (not shown) can be inserted into the body to withdraw the tabs 30a,b to a location outside the body. As shown in FIG. 4C, in some embodiments the tabs 30a,b can be removed from the body without re-penetrating the labrum 4. For example, the tabs 30a,b can be withdrawn around a side of the tissue to be re-attached, rather than through it.

Figure 4D:
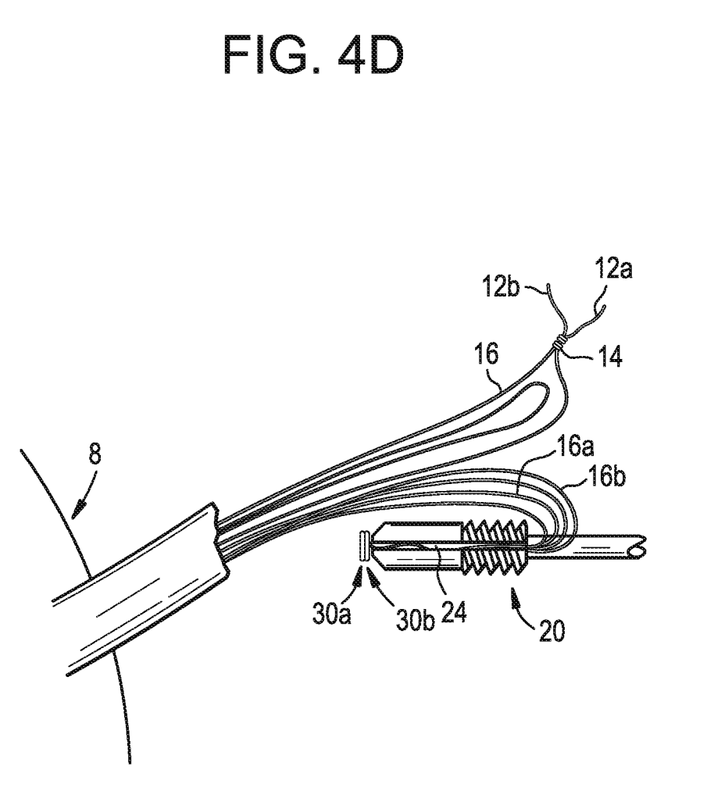
FIG. 4D is a partial cross-sectional representation of the first and second engagement members of the tissue anchor system of FIG. 1 being coupled to the anchor member of FIG. 2.

As shown in FIG. 4D, after withdrawing the tabs 30a,b to a location outside the body, the tabs 30a,b can be coupled to a bone anchor 20 in a manner previously discussed herein. By way of example, the tabs 30a,b can threaded through a lumen of the bone anchor 20. In some embodiments, the portion of the suture loop 16c extending between the first and second tabs 30a,b can be threaded through the bone anchor 20. With the tabs 30a,b coupled to the bone anchor (e.g., at its distal end 20b), the bone anchor 20 can be reinserted into the body and implanted into the bone tunnel 6. Alternatively, as discussed above, the bone anchor 20 can be reinserted into the body and implanted into the bone tunnel 6 with the tabs 30a,b disposed therein (e.g., within the lumen 24 as discussed above in reference to FIG. 5).

Figure 4E:
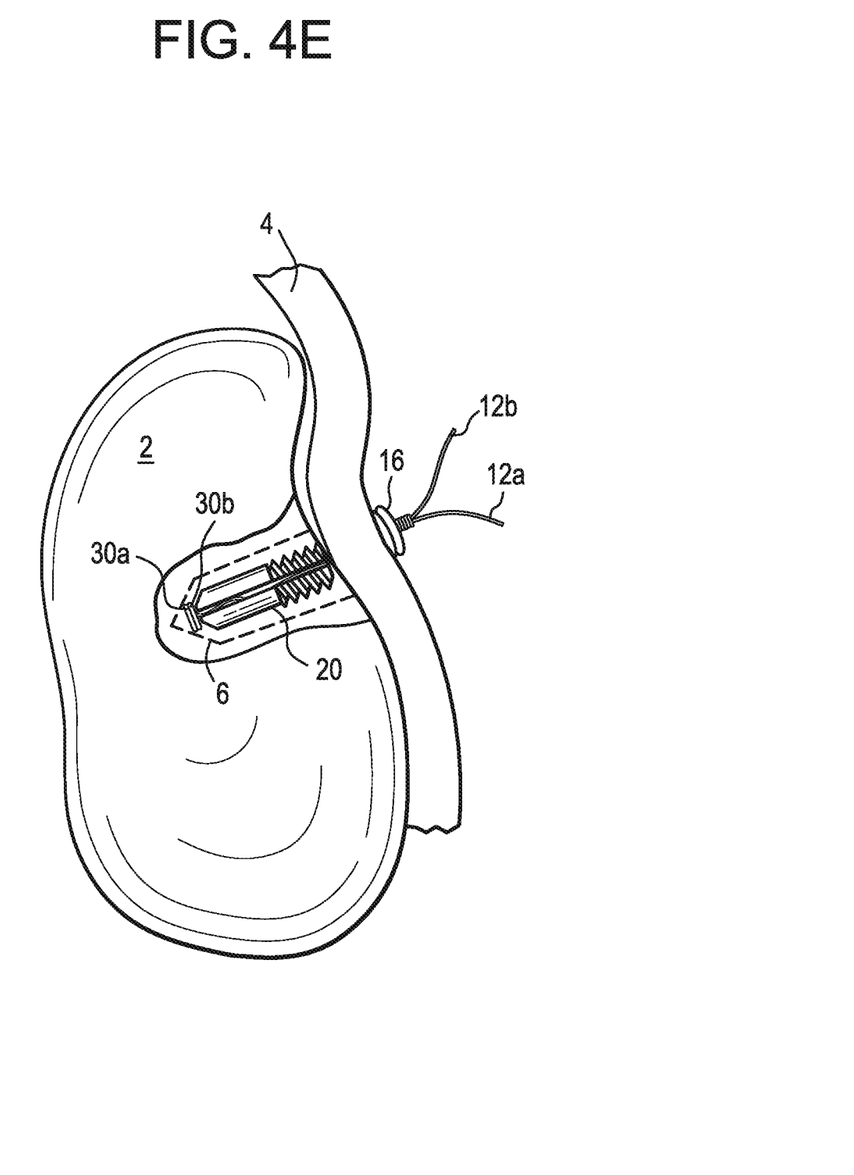
FIG. 4E is a partial cross-sectional representation of the bone anchor of FIG. 2 disposed in a bone hole and with the tissue anchor system of FIG. 1 secured thereto.

By way example, the bone anchor 20 can be inserted into the bone tunnel 6 without penetrating the labrum 4. For example, the bone anchor 20 can be advanced beyond the labrum 4 and into the bone tunnel 6 on the same side of the tissue 4 around which the tabs 30a,b, were withdrawn, in accord with some embodiments as discussed above. After implantation of the bone anchor 20, the sliding knot 14 can be advanced along the suture and toward the labrum 4 to anchor the labrum 4 to the glenoid 2, as shown in FIG. 4E. By way of example, advancing the sliding knot can be effective to shorten the length of the suture loop 16. In various embodiments, the suture 12 can be tensioned until the labrum 4 is re-approximated in its desired position. Once the suture 12 has been tensioned, for example, the terminal ends 12a,b of the suture 12 extending from the sliding knot 14 can be cut.

As will be appreciated by a person skilled in the art, the above-described exemplary technique can result, for example, in the sliding knot 14 being disposed on an opposed side of the labrum 4 from the tabs 30a,b and the bone anchor 20 when the labrum 4 is reattached to the glenoid 2. It should be further appreciated that the above-described exemplary technique can result in a "mattress stitch," in which a portion of the suture loop 16c can extend from a first tab 30a to an internal surface of the labrum 4 (i.e., on the surface of the labrum 4 adjacent the glenoid 2), through the labrum 4 to an external surface thereof, back through the labrum 4 at an adjacent location to emerge from the labrum's internal surface, and to a second tab 30b.

It will also be appreciated that devices and methods in accord with the teaching herein can be effective to apply, for example, a "simple stitch" to anchor the labrum 4 to the glenoid 2. In such a technique, the tab 30a can be advanced through the labrum 4, withdrawn to a location outside the body, and coupled to the anchor 20, substantially as described above with reference to FIGS. 4A-4D. The technique differs in that the second tab 30b can be coupled to the bone anchor 20 and subsequently implanted in the bone tunnel 6 without being advanced through the labrum 4. As such, a portion of the suture loop 16c can extend from a first tab 30a to an internal surface of the labrum 4, through the labrum 4 to an external surface thereof, around an edge of the labrum 4, and to a second tab 30b.

The exemplary method described above with reference to FIGS. 4A-4E is but one exemplary method in accord with the present teachings. As will be appreciated by a person skilled in the art, the order of the various steps can be altered, and more or fewer steps than those described can be used to anchor tissue to bone. For example, though FIG. 4D depicts the coupling of the tabs 30a,b to the bone anchor 20 after the tabs 30a,b are withdrawn from the body, in some embodiments, the tabs 30a,b can be coupled to the bone anchor 20 before being withdrawn from the body or can remain in the body after passing through the tissue 4 and can be coupled to the bone anchor 20 after the bone anchor has been implanted in a bone hole 6.

Though the exemplary method illustrated in FIGS. 4A-4E depict the tissue anchor system 10 being coupled to the bone anchor 20 via engagement between the tabs 30a,b and the bone anchor 20, the exemplary method described above can also be performed by directly delivering through tissue portions of the suture loop without an engagement member coupled thereto. For example, as described above with reference to FIG. 3, the bone anchor 320 can include a suture-engaging element (e.g., post 326) that can directly engage the suture. Accordingly, in such an embodiment, segments of the suture loop 316 can be advanced through tissue, retrieved (e.g., withdrawn outside the body), and coupled directly to the bone anchor 320, as otherwise discussed herein.

A person skilled in the art will further appreciate that the tissue anchor systems described herein can have a variety of other configurations, and that a variety of other techniques can be used to re-approximate torn or damaged tissue. Moreover, while the above-described system and methods are described as having only one bone anchor (e.g., a single re-attachment point), the systems and methods described herein can be used with any number of bone anchors. In such a manner, the same or different lengths of suture can be used to couple to multiple bone anchors.

One skilled in the art will appreciate further features and advantages of the presently disclosed method and system based on the above-described embodiments. Accordingly, the present disclosure is not to be limited by what has been particularly shown and described, except as indicated by the appended claims. All publications and references cited herein are expressly incorporated herein by reference in their entirety.

What is claimed is:
1. A method for anchoring tissue to bone, comprising:
   forming an incision in a patient's body;
   utilizing a suture loop having terminal ends attached to one another by a sliding knot;

advancing a first segment of the loop through tissue at a first location within the patient's body as defined by a skin surface of the patient;

withdrawing a portion of the first segment of the loop to a second location external to the skin surface with the first segment of the loop extending through the tissue, the second location being such that, prior to the incision being formed, the second location is external to the skin surface;

coupling the first segment of the loop to a first suture suture-engaging post of a bone anchor that extends from a first portion of an inner sidewall of the anchor that defines a longitudinal bore of the anchor extending from a proximal end of the anchor to a distal end of the anchor, the first suture-engaging post having a proximal-most end in contact with the first portion of the inner sidewall of the anchor and a distal-most end that is on an opposite side of the first suture-engaging post than the proximal-most end and is the portion of the first suture-engaging post that is most proximate to a central longitudinal axis extending through the longitudinal bore of the anchor, the first suture-engaging post extending distally towards the distal end of the anchor from the proximal-most end of the first suture-engaging post to the distal-most end of the first suture-engaging post such that the first segment travels along a distal-facing surface of the first suture-engaging post, towards the proximal-most end of the first suture-engaging post, to be received within a first suture-receiving cavity formed between the distal-facing surface of the first suture-engaging post and the inner sidewall of the bone anchor;

coupling a second segment of the loop to one of:
  the first suture-engaging post of the bone anchor such that the second segment travels along the distal-facing surface of the first suture-engaging post, towards the proximal-most end of the first suture-engaging post, to be received within the first suture-receiving cavity formed between the distal-facing surface of the first suture-engaging post and the inner sidewall of the bone anchor; or
  a second suture-engaging post of the bone anchor that extends from a second portion of the inner sidewall of the anchor that is opposed to the first portion of the inner sidewall, the second suture-engaging post having a proximal-most end in contact with the second portion of the inner sidewall of the anchor and a distal-most end that is on an opposite side of the second suture-engaging post than the proximal-most end and is the portion of the second suture-engaging post that is most proximate to the central longitudinal axis extending through the longitudinal bore of the anchor, the second suture-engaging post extending distally towards the distal end of the anchor from the proximal-most end of the second suture-engaging post to the distal-most end of the second suture-engaging post such that the second segment travels along a distal-facing surface of the second suture-engaging post, towards the proximal-most end of the second suture-engaging post, to be received within a second suture-receiving cavity formed between the distal-facing surface of the second suture-engaging post and the inner sidewall of the bone anchor;

implanting the bone anchor, with the first and second segments coupled thereto, in bone; and advancing the sliding knot toward the tissue to shorten the suture loop.

2. The method of claim 1, wherein coupling the first and second segments to the bone anchor comprises threading the first and second segments through the bone anchor.

3. The method of claim 1, wherein at least one of coupling the first segment of the loop to the bone anchor and coupling a second segment of the loop to the bone anchor is performed outside of the patient's body as defined by the skin surface of the patient.

4. A method for anchoring tissue to bone, comprising:
utilizing a suture loop having terminal ends attached to one another by a sliding knot;

advancing a first segment of the loop through tissue at a first location within a patient's body;

coupling the first segment of the loop to a first suture-engaging post of a bone anchor that extends from a first portion of an inner sidewall of the anchor that defines a longitudinal bore of the anchor extending from a proximal end of the anchor to a distal end of the anchor, the first suture-engaging post having a proximal-most end in contact with the first portion of the inner sidewall of the anchor and a distal-most end that is on an opposite side of the first suture-engaging post than the proximal-most end and is the portion of the first suture-engaging post that is most proximate to a central longitudinal axis extending through the longitudinal bore of the anchor, the first suture-engaging post extending distally towards the distal end of the anchor from the proximal-most end of the first suture-engaging post to the distal-most end of the first suture-engaging post such that the first segment travels along a distal-facing surface of the first suture-engaging post, towards the proximal-most end of the first suture-engaging post, to be received within a first suture-receiving cavity formed between the distal-facing surface of the first suture-engaging post and the inner sidewall of the bone anchor;

coupling a second segment of the loop to one of:
  the first suture-engaging post of the bone anchor such that the second segment travels along the distal-facing surface of the first suture-engaging post, towards the proximal-most end of the first suture-engaging post, to be received within the first suture-receiving cavity formed between the distal-facing surface of the first suture-engaging post and the inner sidewall of the bone anchor; or;
  a second suture-engaging post of the bone anchor that extends from a second portion of the inner sidewall of the anchor that is opposed to the first portion of the inner sidewall, the second suture-engaging post having a proximal-most end in contact with the second portion of the inner sidewall of the anchor and a distal-most end that is on an opposite side of the second suture-engaging post than the proximal-most end and is the portion of the second suture-engaging post that is most proximate to the central longitudinal axis extending through the longitudinal bore of the anchor, the second suture-engaging post extending distally towards the distal end of the anchor from the proximal-most end of the second suture-engaging post to the distal-most end of the second suture-engaging post such that the second segment travels along a distal-facing surface of the second suture-engaging post, towards the proximal-most end of the second suture-engaging post, to be received within a second suture-receiving cavity formed between the distal-facing surface of the second suture-engaging post and the inner sidewall of the bone anchor;

implanting the bone anchor, with the first and second segments coupled thereto, in bone; and advancing the sliding knot toward the tissue to shorten the suture loop.

5. The method of claim 4, further comprising withdrawing a portion of the first segment of the loop to a position outside of the patient's body with the first segment of the loop extending through the tissue.

6. The method of claim 4, wherein the suture-engaging element comprises a post that extends towards the distal end of the bone anchor.

7. The method of claim 6, wherein the post is disposed at an oblique angle with respect to the sidewall.

8. The method of claim 4, wherein coupling the first and second segments to the suture-engaging element further comprises exerting tension on the suture loop to pull the suture loop within a suture-receiving cavity that is located between the suture-engaging element and the sidewall of the lumen.

9. A method for anchoring tissue to bone, comprising:

utilizing a suture loop having terminal ends attached to one another by a sliding knot;

advancing a first segment of the loop through tissue at a first location within a patient's body;

coupling the first segment of the loop to a post that extends from a sidewall of a bone anchor, the bone anchor having a proximal end defined by a threaded outer surface and a distal end defined by a substantially non-threaded outer surface, the first segment of the loop being coupled to a portion of the post that extends into the distal end of the bone anchor, the sidewall defining a lumen that extends between opposed proximal and distal ends of the bone anchor;

coupling a second segment of the loop to the bone anchor;

implanting the bone anchor, with the first and second segments coupled thereto, in bone; and advancing the sliding knot toward the tissue to shorten the suture loop, wherein the sliding knot is disposed proximal of the proximal end of the bone anchor, and proximal of the tissue through which the first segment of the loop is advanced: after the first and second segments of the loop have been coupled to the bone anchor; when implanting the bone anchor in bone; and during and after advancing the sliding knot towards the tissue to shorten the suture loop, the proximal end of the bone anchor being more proximate to the tissue than the distal end of the bone anchor is to the tissue after implanting the bone anchor in bone.

10. The method of claim 9, further comprising withdrawing a portion of the first segment of the loop to a position outside of the patient's body with the first segment of the loop extending through the tissue.

11. The method of claim 9, wherein coupling the first and second segments to the bone anchor comprises threading the first and second segments through the bone anchor.

12. The method of claim 9, wherein at least one of coupling the first segment of the loop to the bone anchor and coupling a second segment of the loop to the bone anchor is performed outside of the patient's body as defined by the skin surface of the patient.

* * * * *